(12) United States Patent
Mantelmacher

(10) Patent No.: US 7,883,547 B2
(45) Date of Patent: Feb. 8, 2011

(54) ANTI-SLIP PROSTHETIC ATTACHMENT SYSTEM

(76) Inventor: H Lee Mantelmacher, 3704 Ashley Way, Owings Mills, MD (US) 21117

( * ) Notice: Subject to any disclaimer, the term of this patent is extended or adjusted under 35 U.S.C. 154(b) by 0 days.

(21) Appl. No.: 12/589,393

(22) Filed: Oct. 22, 2009

(65) Prior Publication Data

US 2010/0121464 A1   May 13, 2010

Related U.S. Application Data

(63) Continuation-in-part of application No. 11/496,707, filed on Jul. 31, 2006, now Pat. No. 7,771,487.

(60) Provisional application No. 61/196,989, filed on Oct. 22, 2008.

(51) Int. Cl.
*A61F 2/80* (2006.01)
(52) U.S. Cl. ......................................... 623/34
(58) Field of Classification Search ............. 623/32–37
See application file for complete search history.

(56) References Cited

U.S. PATENT DOCUMENTS

| | | | | |
|---|---|---|---|---|
| 4,842,608 A * | 6/1989 | Marx et al. | ..... | 623/33 |
| 5,653,766 A * | 8/1997 | Naser | ..... | 623/33 |
| 7,727,284 B2 * | 6/2010 | Warila | ..... | 623/36 |
| 7,771,487 B2 * | 8/2010 | Mantelmacher | ..... | 623/34 |

* cited by examiner

*Primary Examiner*—Bruce E Snow
(74) *Attorney, Agent, or Firm*—Ober, Kaler, Grimes & Shriver; Royal W. Craig

(57) ABSTRACT

An anchoring system for a transtibial or transfemoral (above or below the knee) prosthesis. The anchoring system includes a liner for enveloping an amputee limb. The liner has a first strap attached toward an upper end, and a corresponding strap fixedly attached to the distal bottom end of the liner. The anchoring system also includes a containment socket for seating the liner. The containment socket has a pair of slots there through at positions corresponding to the two straps of the liner, respectively. To apply the anchoring system, the patient first applies the liner to his/her limb. The liner is then inserted into the socket with the two fastening straps protruding out through the respective slots. The patient pulls down on the lower strap thereby drawing the liner down into the socket until the liner is securely seated in the socket. When fully seated, the two fastening straps are overlayed and secured to themselves by Velcro™. The foregoing forms a suspension which holds the prosthesis on. Moreover, the fastening straps through slots absolutely prevent lateral shift as well as rotation.

1 Claim, 4 Drawing Sheets

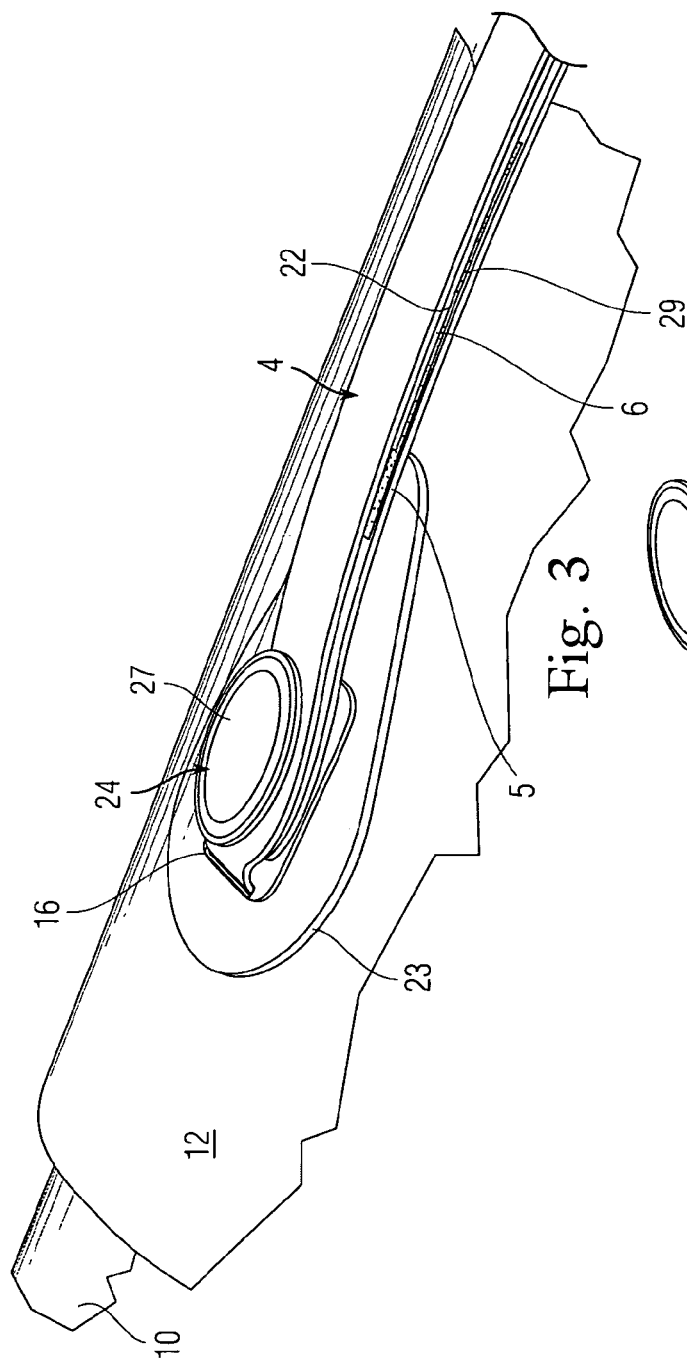
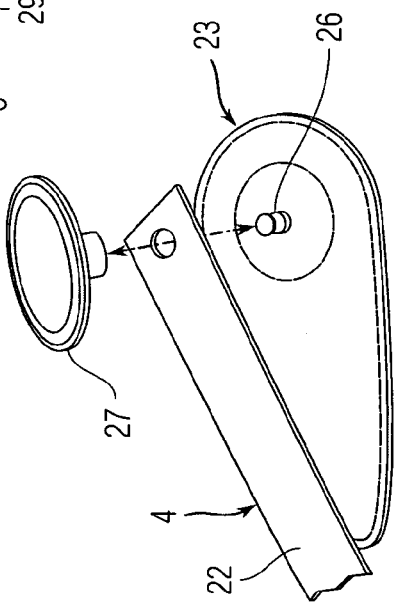
Fig. 3
Fig. 4

ANTI-SLIP PROSTHETIC ATTACHMENT SYSTEM

CROSS-REFERENCE TO RELATED APPLICATION(S)

The present application derives priority from U.S. provisional application Ser. No. 61/196,989 filed Oct. 22, 2008, and is a continuation-in-part of U.S. application Ser. No. 11/496,707 filed Jul. 31, 2006 now U.S. Pat. No. 7,771,487.

BACKGROUND OF THE INVENTION

1. Field of the Invention

The present invention relates to prosthetics and, more particularly, to an anchoring system for post-operative prosthetic devices for above-the-knee amputation patients.

2. Description of the Background

There are a variety of different types of prosthetic devices for patients that have had either transfemoral (above-knee) or transtibial (below the knee) amputation. Typically, post-operative prosthetic devices for either type of amputation patients begin with a liner, which is rolled on to the residual limb. The liner is a soft, stretchy material that acts as an interface with the prosthetic.

Once the liner is on, the residual limb then slides into a hard socket. This socket is specially made to fit and can be made out of a variety of materials.

The hard socket for a transfemoral prosthesis has a knee joint connected to it, and the more fluid and natural the movement of the knee the better. Transtibial prosthetics have no knee joint. In both cases (with or without a knee joint) there typically is an aluminum or carbon fiber tube to which a foot module is connected.

For example, U.S. Pat. No. 5,653,766 to Naser issued Aug. 5, 1997 shows a prosthetic device 20 having a generally cylindrical socket 24 with an opening for receiving an amputated limb. The socket 24 is closed at the other end, and is mounted on a bendable knee joint. Once the limb is properly received within the socket 24, straps 38 are adjusted so that a secure fit is achieved. The patient then is able to walk using the prosthetic device 20.

With all such transfemoral and/or transtibial prosthetics (above & below the knee), it is very important that the socket be securely fitted to the limb and secured in place. Stability is a common problem as many existing anchoring systems use a single attachment point to hold the residual limb in place, and this typically leads to extraneous pivoting, rotation and shift during ambulation. Moreover, it is important to be able to adjust the anchoring system periodically because the mass of the limb may change significantly over the course of a day. The above-referenced '766 patent uses a radial pressure-fit imposed by tightening two belts. However, this tends to squeeze the limb unevenly and adds to discomfort. Moreover, the radial pressure tends to pop the limb out of the socket over the course of a day.

Another well-known ICEX® Socket System uses a combination lanyard and pin kit as a docking and locking mechanism. The socket has a distal pin that docks with the prosthesis. A lanyard is connected to the liner through a slot in the bottom of the socket. The lanyard is pulled to allow the patient's residual limb, which is enclosed in the silicone liner, to be drawn into the socket by the lanyard. The lanyard is then anchored to the front of the socket. The lanyard has the advantage of allowing for adjustment of position within the ICEX Socket. If the limb changes position because of volume change and the distal migration of the limb into the socket, the prosthesis can easily be adjusted by the lanyard to compensate. The lanyard method of donning the socket also significantly reduces pain directly related to the donning process with a pin-locking mechanism. However, it has been found that many amputees lack the room for, are unable to tolerate, or have difficulty engaging the distal pin. Others complain of pain associated with engagement of the pin.

There are a number of "suspension" type sockets that eliminate the pin. U.S. Pat. No. 6,645,253 to Caspers issued Nov. 11, 2003 shows a suction system that employs a vacuum pump to impart suction to the liner, the vacuum pump doubling as a shock absorber for the artificial limb. Commercially, this is known as the Harmony® System which pulls air from the sealed socket and evacuates moisture (sweat) buildup. A nonporous polyurethane liner (not shown) is fitted over the residual limb and is inserted in the socket. A vacuum pump is attached via a connector block beneath the socket to create a vacuum force which is coupled by a tube to the liner, thereby evacuating air and sealing it to the residual limb. This provides a total-contact hypobaric suction equal weight distribution socket liner which tacks up to the skin of the residual limb and provides total contact with the limb.

U.S. Pat. No. 6,793,682 to Mantelmacher discloses a "Sure-fit Prosthetic Attachment System" (known commercially as the KISS® System) for a transfemoral and/or transtibial prosthesis, comprising a liner for enveloping an amputee limb. The liner has a buckle suspended toward the upper end, and a corresponding strap fixedly attached on the bottom end of the liner. The anchoring system also includes a containment socket for seating the liner. The containment socket has a pair of slots there through at positions corresponding to the buckle and strap of the liner, respectively. To apply the anchoring system, the patient first applies the liner to his/her limb. The liner is then inserted into the socket with the fastening strap and buckle protruding out through the respective slots. The fastening strap is then threaded up through the buckle (running upward along the side of the socket) and are inserted there through. The patient pulls down on the strap and it works by pulley action to draw the liner down into the socket until the liner is securely seated in the socket. When fully seated, the fastening strap is secured to itself by Velcro. The foregoing forms a suspension which holds the prosthesis on. Moreover, the fastening straps through slots absolutely prevent lateral shift as well as rotation. On the other hand, the patient need only readjust the Velcro closure to adjust the position of the limb within the socket. Thus, if the limb changes position because of volume change and the distal migration of the limb into the socket, the prosthesis can easily be adjusted to compensate.

It would be greatly advantageous to modify the above-described KISS® attachment system to provide a dual-lanyard fastening system alongside the socket so that the patient pulls down on one strap to draw the liner down into the socket until the liner is securely seated in the socket, and then the two opposing straps of the dual-lanyard type anchor are attached by Velcro™ to prevent extraneous up and down motion, pivoting, rotation and shift during ambulation.

SUMMARY OF THE INVENTION

Accordingly, it is an object of the present invention to provide a prosthetic anchoring system which increases the stability of the liner anchor using top-side and lower mechanical lanyard-type attachments to prevent all extraneous up and down motion, pivoting, rotation and shift.

It is still another object to provide a prosthetic anchoring system as described above that remains easy to put on, and to readjust/tighten the fit of the liner in the socket from a sitting position.

In accordance with the foregoing object, the present device comprises an anchoring system for a transfemoral and/or transtibial prosthesis, comprising a liner for enveloping an amputee limb. The liner has a first strap attached toward an upper end, and a corresponding strap fixedly attached to the distal bottom end of the liner. The anchoring system also includes a containment socket for seating the liner. The containment socket has a pair of slots there through at positions corresponding to the two straps of the liner, respectively. To apply the anchoring system, the patient first applies the liner to his/her limb. The liner is then inserted into the socket with the two fastening straps protruding out through the respective slots. The patient pulls down on the lower strap thereby drawing the liner down into the socket until the liner is securely seated in the socket. When fully seated, the two fastening straps are overlayed and secured to themselves by Velcro™

The foregoing forms a suspension which holds the prosthesis on. Moreover, the fastening straps through slots absolutely prevent lateral shift as well as rotation. On the other hand, the patient need only readjust the Velcro closure to adjust the position of the limb within the socket. Thus, if the limb changes position because of volume change and the distal migration of the limb into the socket, the prosthesis can easily be adjusted to compensate.

BRIEF DESCRIPTION OF THE DRAWINGS

Other objects, features, and advantages of the present invention will become more apparent from the following detailed description of the preferred embodiment and certain modifications thereof, in which:

FIG. 3 is a close-up perspective view of the upper strap anchor 4 attached by grommet 24 to a reinforcement plate 23.

FIG. 4 is a close-up exploded view of the strap anchor 4 and grommet 24 as in FIG. 3.

DETAILED DESCRIPTION OF THE PREFERRED EMBODIMENTS

Figure 1:
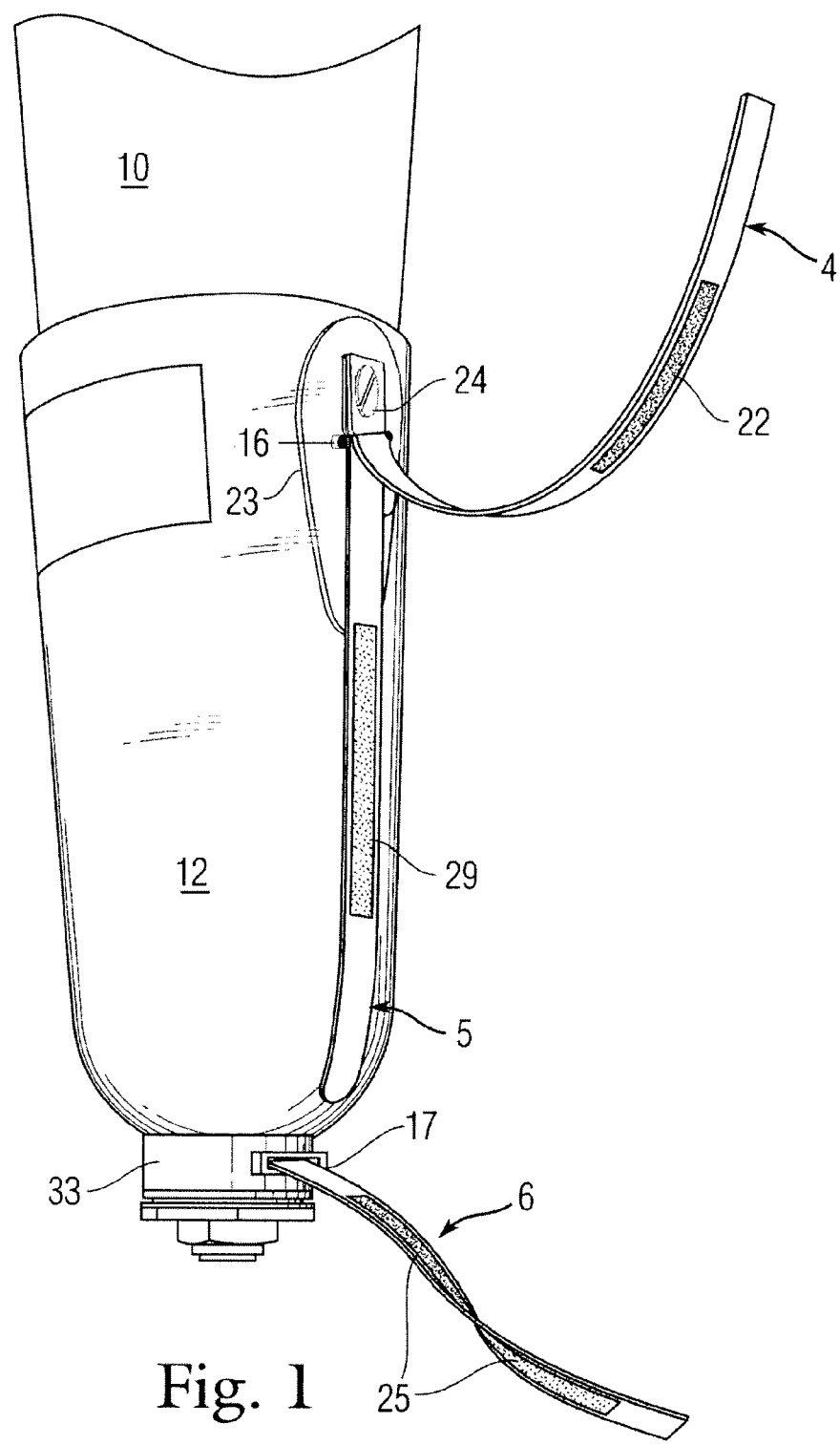
FIG. 1 is a perspective illustration of the prosthetic anchoring system 2 according to one embodiment of the present invention with straps 4, 6 unattached.
Figure 2:
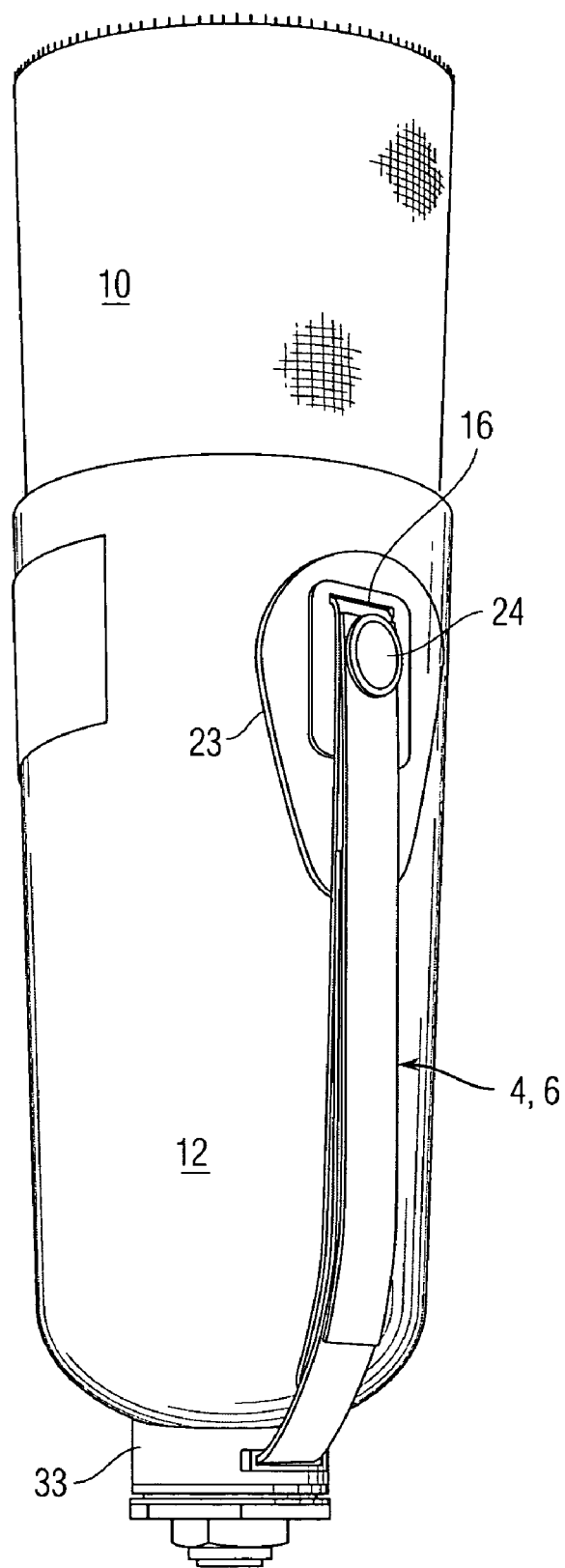
FIG. 2 is a perspective view of the prosthetic anchoring system 2 as in FIG. 1 with straps 4, 6 attached.

The present invention is a prosthetic attachment system for transfemoral and transtibial (above-knee and below-knee) amputees. FIG. 1 is a perspective illustration of the prosthetic anchoring system 2 according to one embodiment of the present invention with straps 4, 6 unattached, and FIG. 2 is a perspective view with straps 4, 6 attached.

The anchoring system 2 generally includes a commercially-available liner 10 equipped with upper and lower strap-anchors 4, 6, respectively, in accordance with the present invention. The upper strap anchor 4 is pivotally attached at one end by grommet 24 to a reinforcement plate 23, plate 23 being a plastic member that is sewn and/or bonded peripherally with adhesive or Velcro™ onto the liner 10 at an upper outside position as shown. In addition, a lower strap 6 is attached at one end to the bottom of the liner 10. The liner 10 fits within a molded socket 12 and rests upon a centering cup 33. The lower fastening strap 6 is provided with a length of hook-and-loop (Velcro™) material 25 along its backside and extending out to the distal end.

Similarly, the upper fastening strap 4 is provided with a length of hook-and-loop material 22 along its inside and extending down to the distal end. The socket 12 is also provided with a length of hook-and-loop material 29 running between the reinforcement plate 23 and centering cup 33.

A patient applies the liner 10 to their limb and inserts the liner 10 into the socket 12. The lower fastening strap 6 is threaded out through centering cup 33 and through lower slot 17, while upper strap 4 is passed out through upper slot 16. The lower fastening strap 6 is pulled out tight, and by its section of hook-and-loop material 25 it is releasably joined to the opposing hook-and-loop material 29 on the socket fastening strap 5. Then the upper fastening strap 4 is pulled down tight, and by its section of hook-and-loop material 22 it is releasably joined to the opposing hook-and-loop material 25 on the lower fastening strap 6. This forms a suspension which holds the prosthesis on and absolutely prevents lateral movement, pivotal shifting, and rotation. The particular components of the anchoring system 2 will now be described in more detail with reference to FIGS. 3-4.

FIG. 3 is a close-up perspective view of the upper fastening strap 4 attached by grommet 24 to a reinforcement plate 23, and FIG. 4 is a close-up exploded view of the upper fastening strap 4 and grommet 24. With combined reference to FIGS. 1-4, the socket 12 is formed with at least one slot 16 passing through an upper side (at the outside of the limb) for allowing the upper strap 4 to pass outwardly there from.

Referring back to FIG. 1, the socket 12 is also formed with one lower slot 17 at the bottom and aligned with the upper slot 16 for allowing the lower strap 6 to pass outwardly there from.

In use, the patient would first apply liner 10 to limb. The liner 10 is then inserted into the socket 12 with lower fastening strap 6 threaded through centering cup 33 out through lower slot 17, and upper strap 4 passing out through upper slot 16. The lower fastening strap 6 is pulled tight until the liner 10 is securely seated in the socket 12 atop cup 33. The lower fastening strap 6 is secured onto the Velcro™ 29 on the socket 12, and is then sandwiched by overlying it with the upper strap 4 by joining their opposing sections 22, 25 of hook-and-loop material. The foregoing forms a suspension which holds the prosthesis on and absolutely prevents lateral movement, pivotal shifting, and rotation. On the other hand, the simple Velcro™ attached strap 6 allows for convenient adjustment of the position of the limb within the socket 12. Thus, if the limb changes position because of volume change and the distal migration of the limb into the socket, the prosthesis can easily be adjusted by adjusting straps 4, 6 to compensate.

Liner 10 is largely a standard transfemoral or transtibial suspension liner designed for amputees with amputations along the length of the tibia or femur. There are a variety of commercially-available suspension liners which will suffice, provided that they afford good suspension independent of volume fluctuations and provide a comfortable anatomical fit. These liners are typically formed of silicone or a gel blend with a fabric shell, and they may be equipped with a threaded socket assembly at the bottom for screw-insertion of a pin such as utilized in prior art pin securing assemblies. In accordance with the present invention, the otherwise conventional liner is modified by securing the strap 4 and reinforcement plate 23 on the outwardly facing side of the liner 10. The reinforcement pad 23 is sewn and/or adhered peripherally to the shell of the liner 10. Presently, the grommet 24 comprises two screw-together sections including a post 26 and cap 27 each having 1" flanges that sandwich the upper strap 4 there between. The pad 23 is comprised of an oval section of reinforced vinyl or similar material, with a hole in it for post 26, which can be glued to the liner 10, or may be backed with hook and loop Velcro™ to adhere to liner 10. Upper strap 4 is hole-punched at the distal end and is inserted over the post 26, and the cap 27 is applied to secure the strap 4 on the post 26.

Both upper and lower fastening straps 4, 6 comprise approximately a 6-8" length of Nylon™ or Dacron™ braided strap, the lower strap 6 having opposing sections 25 of hook and loop material running to the respective tips on both sides, and the upper strap 4 having one section 22 of hook and loop material running to the respective tips on the inside. The lower fastening strap 6 is attached at one end to the bottom of liner 10. For example, existing liners may be equipped with a threaded socket assembly at the bottom end as shown and described in the '682 patent to Mantelmacher, which can be used to pivotally anchor the strap 4 thereto.

Figure 5:
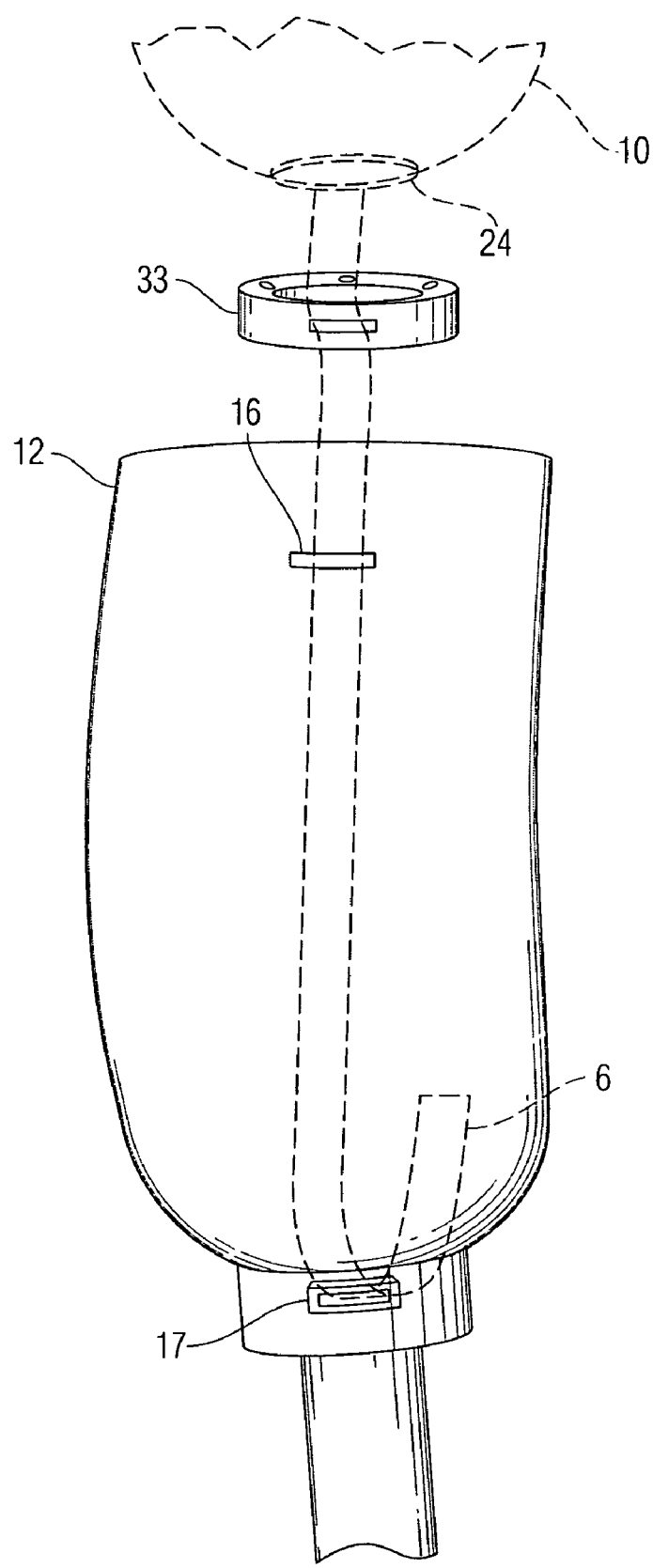
FIG. 5 is a close-up perspective view of the socket 12.

FIG. 5 is a close-up perspective view of the socket 12. Socket 12 is generally a conventional socket formed of flexible plastic that is vacuum formed. The socket 12 made in a custom-fitted component that is made in a conventional manner of a copolymer plastic, plastic polypropylene, polyester, acrylic/epoxy resin. The socket 12 may be vacuum formed or thermoformed by heating the plastic material and forming it over a mold. In accordance with the present invention the socket 12 is formed with a pass-through slot 16 upwardly along the outside. The slot 16 is spaced with respect to the liner 10 so that when inserted therein it is aligned with the upper strap 4. Specifically, when the liner 10 is fully inserted the pass-through slot 16 should be even with the grommet-post 24 on liner 10. This allows the upper strap 4 (not shown) to be inserted directly through the slot 16 from inside the socket 12 to outside, such that downward tension on strap 4 anchors the grommet-post 24 directly against the slot. In addition to the upper slot 16, a lower pass-though slot 17 is positioned downwardly along the same side of the socket 12. The lower pass-through slot 17 is spaced in the bottom of the socket 12 at the centering cup 33 exit. This way, when the liner 10 is fully inserted the pass-through slot 17 allows the lower fastening strap 6 to be inserted there through. The outer end of the socket 12 is adapted to be connected to a conventional, bendable knee joint (a variety of which are presently available).

To apply the anchoring system 2, the patient first applies the liner 10 to his/her residual limb. The liner 10 is then partially inserted into the socket 12 until lower fastening strap 6 can be threaded through the slot 38 in centering cup 33 and on outward through the lower slot 17 through socket 12. In addition, the upper fastening strap 4 is passed outward through upper slot 16. The patient pulls down on the distal end of upper strap 4 which draws the liner 10 down into the socket 12 until the liner 10 is securely seated in the socket 12. When fully seated, the upper fastening strap 4 is overlayed atop the lower fastening strap 6 and is secured thereto by the opposing hook and loop sections 22, 25.

The foregoing forms a suspension which holds the prosthesis on. Moreover, the fastening strap 6 through lower slot 17 forms a first anchoring point, and the upper strap 4 through upper slot 16 forms a second anchoring point, the combination of the two anchoring points serving to absolutely prevent lateral movement, pivotal and proximal shift, and rotation. On the other hand, the patient need only readjust the hook and loop (Velcro™) closure to adjust the position of the limb within the socket 12. Thus, if the limb changes position because of volume change and the distal migration of the limb into the socket, the prosthesis can easily be adjusted to compensate.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. An anchoring system for a prosthesis, comprising:
   a liner for enveloping an amputee limb, said liner having a first strap attached proximate an upper end of said liner, and a section of hook and loop material on said first strap, and a second strap attached at a lower end of said liner, said second strap having and a section of hook and loop material on said second strap for fastening said second strap onto the first strap;
   a socket for receiving said liner, said socket having a first slot there through at a position corresponding to the first strap and a second slot there through at a position corresponding to the second strap, and a section of hook and loop material between said slots.

* * * * *